United States Patent [19]

Jones et al.

[11] Patent Number: 5,124,127
[45] Date of Patent: Jun. 23, 1992

[54] HOLLOW FIBER BLOOD OXYGENATOR

[75] Inventors: Kenneth A. Jones, Lake Elsinore; Francis M. Servas, San Juan Capistrano; Timothy C. Ryan; Gregory G. Ulrich, both of Mission Viejo, all of Calif.

[73] Assignee: Shiley, Incorporated, Irvine, Calif.

[21] Appl. No.: 302,422

[22] Filed: Jan. 26, 1989

[51] Int. Cl.$^5$ .................................. A61M 1/14
[52] U.S. Cl. ........................... 422/46; 422/48; 210/321.74; 210/321.79; 210/321.83; 210/321.88; 210/487; 210/497.1; 55/16; 55/158; 128/DIG. 3; 261/DIG. 28
[58] Field of Search ............... 422/46, 48; 210/321.74, 210/321.79, 321.83, 321.88, 487, 497.1; 55/16, 158; 128/DIG. 3; 261/DIG. 28

[56] References Cited

U.S. PATENT DOCUMENTS

| | | | |
|---|---|---|---|
| 3,074,401 | 1/1963 | Friedman et al. | 128/214 |
| 3,422,008 | 1/1969 | McLain | 210/22 |
| 3,794,468 | 2/1974 | Leonard | 55/158 X |
| 3,856,475 | 12/1974 | Marx | 55/16 X |
| 4,110,220 | 8/1978 | Lavgender | 210/456 |
| 4,207,192 | 6/1980 | Coplan et al. | 55/158 X |
| 4,239,729 | 12/1980 | Hasegawa et al. | 422/48 |
| 4,242,203 | 12/1980 | Amicel et al. | 210/321.1 |
| 4,265,303 | 5/1981 | Giurtino et al. | 165/166 |
| 4,293,418 | 10/1981 | Fujii et al. | 210/321.1 |
| 4,312,757 | 1/1982 | Brumfield | 210/646 |
| 4,368,124 | 1/1983 | Brumfield | 210/321.3 |
| 4,374,802 | 2/1983 | Fukasawa | 422/48 |
| 4,376,095 | 3/1983 | Hasegawa | 422/46 |
| 4,407,777 | 10/1983 | Wilkinson et al. | 422/46 |
| 4,428,403 | 1/1984 | Lee et al. | 422/46 X |
| 4,476,022 | 10/1984 | Doll | 210/433.2 X |
| 4,620,965 | 11/1986 | Fukasawa et al. | 422/46 |
| 4,639,353 | 1/1987 | Takemura et al. | 422/46 |
| 4,645,645 | 2/1987 | Martinez et al. | 422/46 |
| 4,808,378 | 2/1989 | Nakanishi et al. | 422/48 |

FOREIGN PATENT DOCUMENTS 0187708 7/1986 European Pat. Off.

Primary Examiner—Lynn M. Kummert
Attorney, Agent, or Firm—Knobbe Martens Olson & Bear

[57] ABSTRACT

A hollow fiber blood oxygenator is provided having a plurality of enclosed, coaxial heat exchanger coils, having a common header to insure uniform temperature in the coils. An enclosed fiber bundle is concentrically positioned inside the heat exchanger coils to define a flow path around the coils and through the fiber bundle. The heat exchanger coils and the outside of the fiber bundle are tapered to provide a close fit. Gas manifolds direct gas flow to and from the hollow fibers.

16 Claims, 5 Drawing Sheets

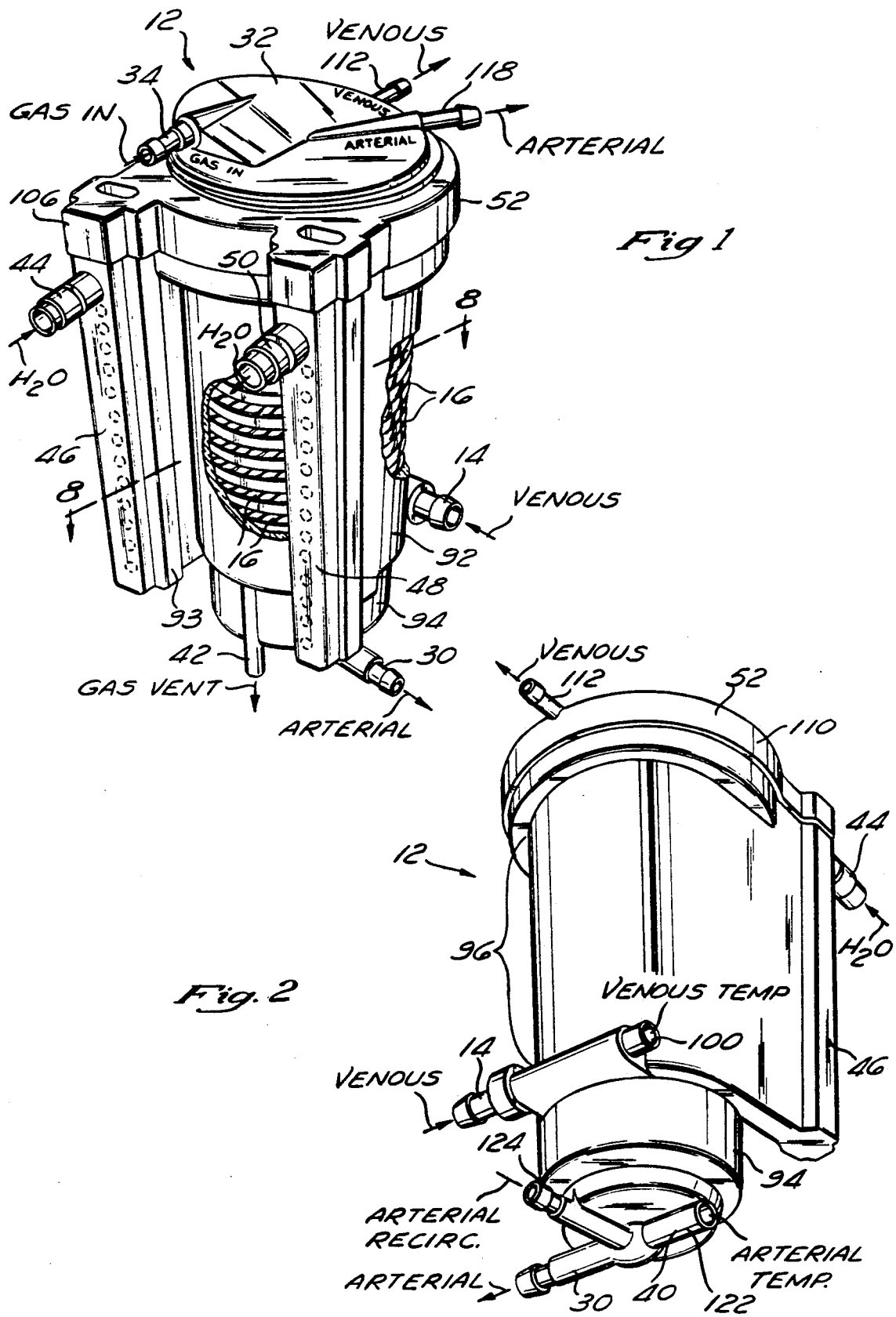

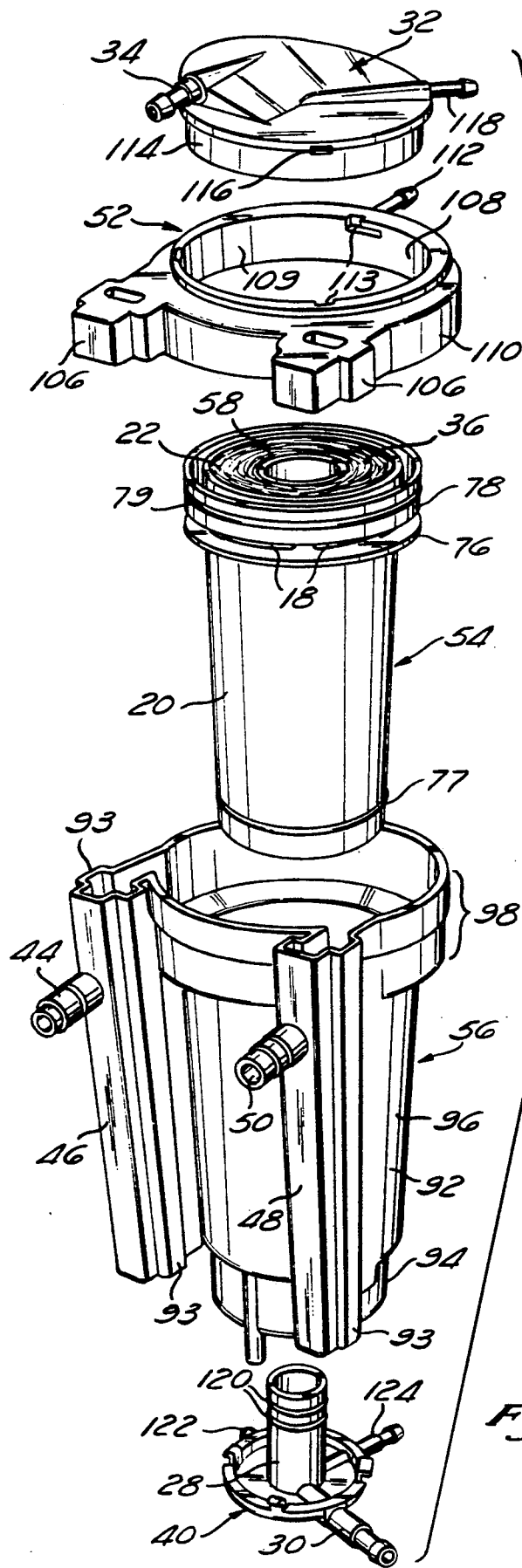
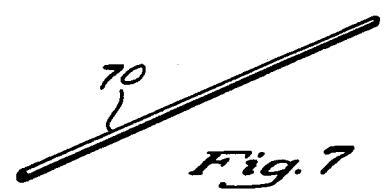
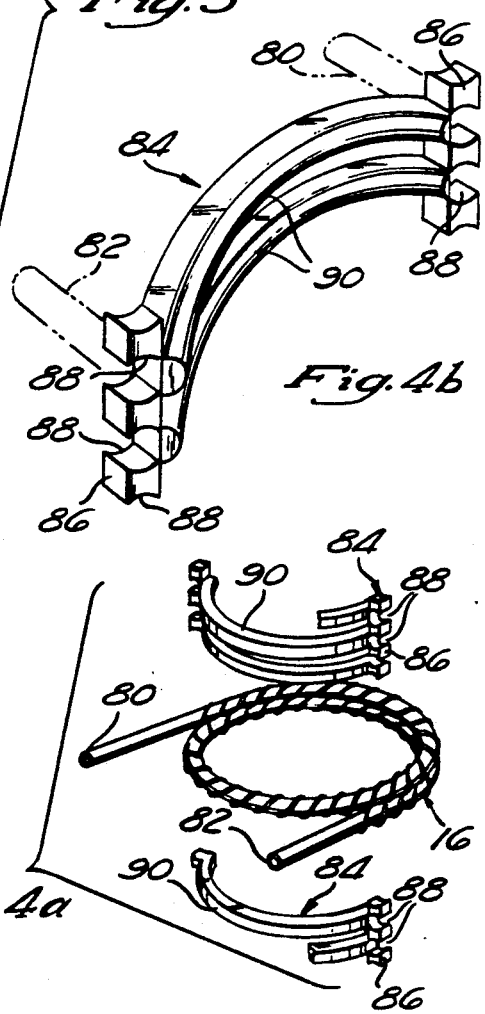

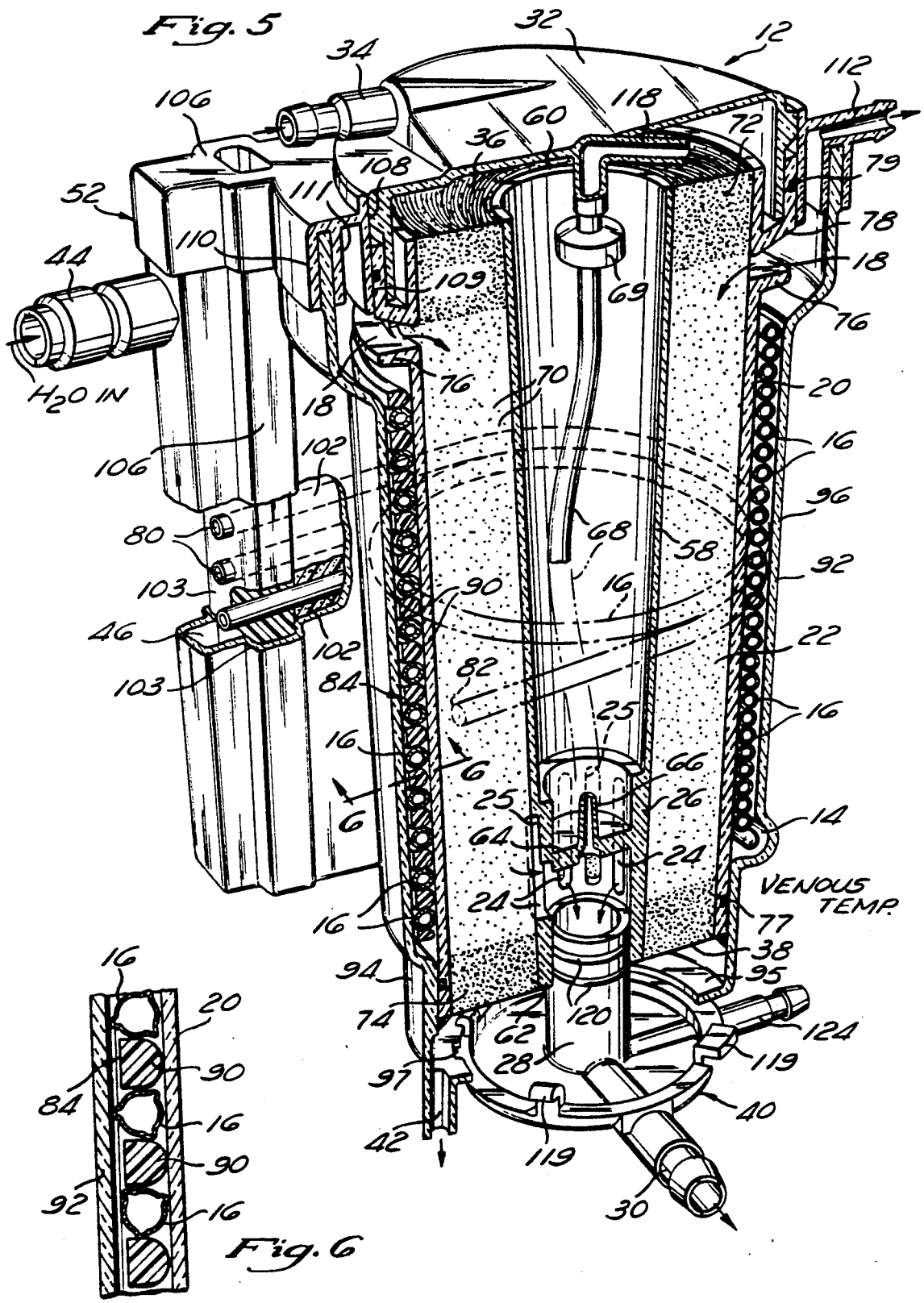

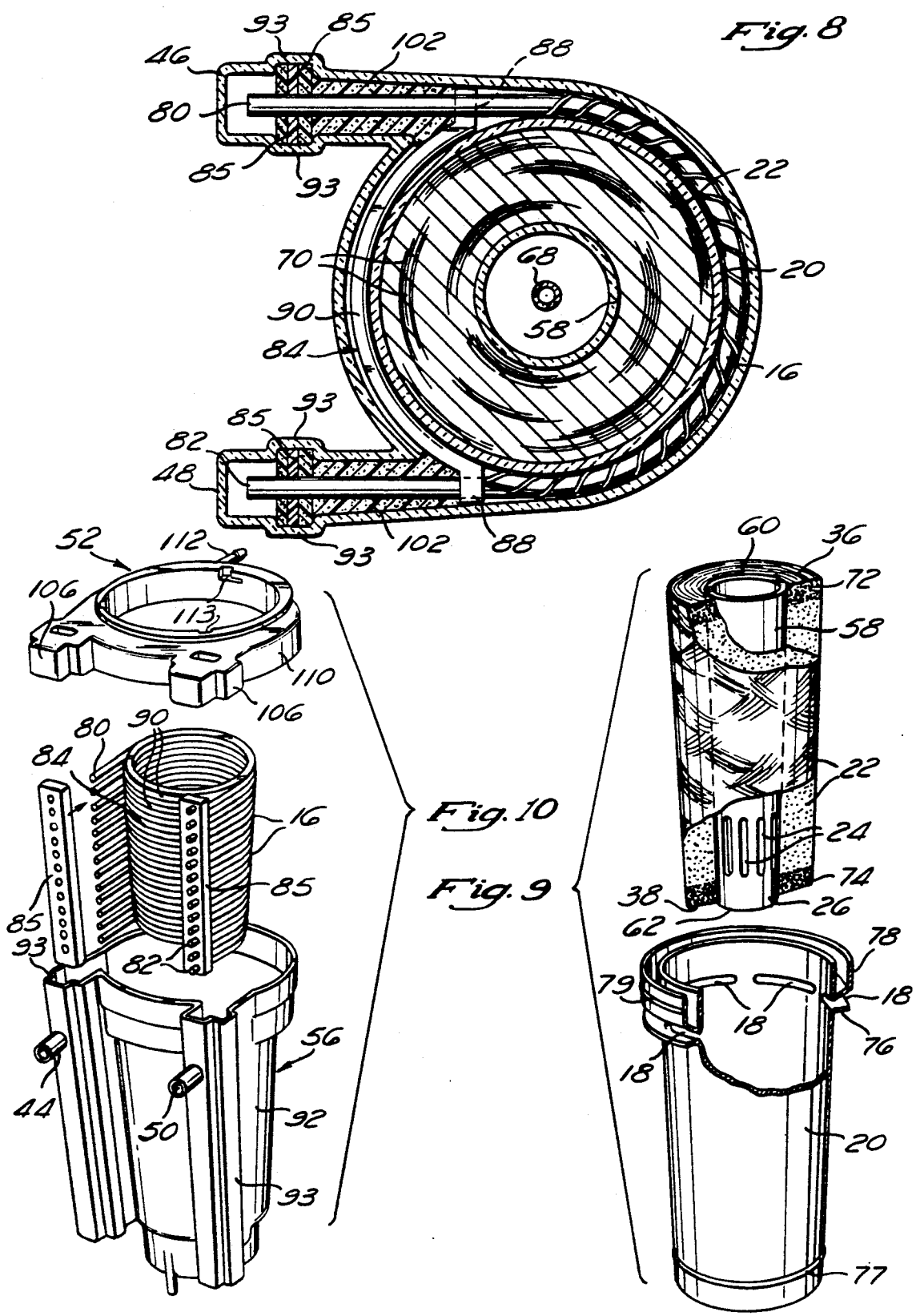

HOLLOW FIBER BLOOD OXYGENATOR

This invention relates generally to the field of blood oxygenators, and specifically to hollow fiber blood oxygenators.

BACKGROUND OF THE INVENTION

Blood oxygenator systems are used in open heart surgery and for providing emergency cardiopulmonary assistance. In both instances, the oxygenator takes over, either partially or completely, the function of removing carbon dioxide from the blood, and replacing it with oxygen, as is normally done by the patient's lungs.

A typical use of a blood oxygenator is shown with respect to FIG. 12, in which venous blood is removed from a patient and placed in a venous reservoir. A blood pump pumps the blood through an oxygenator which replenishes the oxygen in the blood. A heat exchanger adjusts the temperature of the blood to induce hypothermia or to maintain normothermia during surgery. The oxygenated blood then passes through an arterial filter to remove any bubbles, whereupon it is returned to the patient.

Within the oxygenator itself, the venous blood which is depleted in oxygen and enriched in carbon dioxide, is placed in contact with microporous membranes. The membranes have an enriched oxygen gas on one side, and the depleted oxygen blood on the other side of the membrane. Oxygen passes from the gas, through the membrane, into the blood. Concurrently, carbon dioxide passes from the blood, through the membrane, into the oxygen gas. The oxygenated blood is returned to the patient.

There are two types of membrane blood oxygenators currently available. The first type is referred to as a flat plate membrane oxygenator, and employs one or more thin, flat sheets of microporous membrane. Oxygen is placed on one side of the membrane, and oxygen-depleted blood is placed on the other side of the membrane, with the gas transfer taking place across the membrane.

The other type of membrane oxygenator is the hollow fiber oxygenator. This type of oxygenator uses hundreds or thousands of microporous or semi-permeable hollow fibers to achieve the gas transfer. The hollow fibers are sealed in the end walls of a housing such that a gas can be passed through the length of the hollow fibers. Blood is passed around the outside of the fibers with the gas transfer occurring across the walls of the plurality of fibers. In some devices, the blood flows through the hollow fibers with the oxygen gas flowing around the outside of the fibers to achieve the gas transfer.

The hollow fiber blood oxygenators typically have the fibers packed in a cylindrical shaped bundle, with the bundle length and the diameter varying depending upon the amount of gas transfer area desired. The housing into which these cylindrical bundles are placed is sized to correspond to the bundle diameter and length in order to ensure that all of the blood contacts the fibers, and contacts as many fibers as possible. Moreover, a close fit between the fiber bundles and the housing is desirable since it reduces the "priming volume" of fluid needed to fill the housing and fiber bundle and prevents blood from shunting around or bypassing the fiber bundle.

It is difficult, however, to maintain an accurate diameter on the fiber bundles because of the small size and flexibility of the individual fibers. For example, the hollow fibers can have an inside diameter of about 400 microns with a wall thickness of about 25 microns. These fibers are formed into a fiber bundle by winding them onto a core, and during the winding, the fibers may be pulled and stretched resulting in physical dimensional variability. The small size of these fibers thus makes it difficult to maintain accurate dimensions on the diameter of the wound fiber bundles which, in turn, increases manufacturing and assembly costs of blood oxygenators having close tolerances on the fit between the fiber bundle and the housing. There is thus a need to provide a more simple and efficient means for insuring a close fit between the housing and the fiber bundle in order to provide for a low priming volume and prevent blood from bypassing the fibers in the fiber bundle.

A heat exchanger is usually used in conjunction with a blood oxygenator in order to control the temperature of the blood returned to the patient. The heat exchange is typically achieved by passing the blood over a heated surface. There is a need, however, for an efficient, compact heat exchanger having a low priming volume and low flow resistance.

SUMMARY OF THE INVENTION

The present invention provides a combined blood oxygenator and heat exchanger having a compact configuration, low priming volume, and low pressure drop with high oxygenation and heat exchange efficiencies. Moreover, the unit has several subassemblies which are tapered to not only provide an easier and quicker assembly, but to permit the use of less exacting and expensive manufacturing techniques.

Still further, while there are a plurality of individual heat exchanging coils used in the heat exchanger, the temperature in each of the coils is uniform because the heating fluid is provided from a common header or manifold which eliminates hot spots and cold spots in the individual coils.

Still further, a fluid port allowing sampling of the oxygenated blood is provided at the top of the oxygenator, where it is readily accessible. This is a great improvement over the prior versions which required accessing a port on the bottom of the oxygenator with extended contortions and bending to reach the port.

Finally, a means for removably attaching a venous reservoir to the blood oxygenator unit itself is provided. This detachable reservoir allows the use of fewer components during an operation, and allows a common venous reservoir to be used during surgery as well as being used for post-surgery drainage of the wound.

The hollow fiber oxygenator of this invention uses semi-permeable microporous fibers which are wound about a tapered hollow core with the length of the fibers being enclosed within a flow path of the extracorporeal blood. The fibers are wound onto the tapered core, the ends of the core are sealed in potting compound, and after curing the ends are cut perpendicularly in order to expose the ends of each fiber. The respective ends of the fibers are enclosed within a gas manifold for the inlet and outlet of the blood gasses.

The tapered circular periphery of the fibers is enclosed in a correspondingly tapered interior housing, with the tapers insuring a close fit between the housing and fiber bundle. There are apertures at the larger end, or top of the interior housing, and at the small end of the tapered core to allow the passage of extracorporeal blood along the length of the fibers.

An integral heat exchanger comprises an anodized aluminum heat exchanger with a plurality of circular, coaxially arranged coils in which each coil circles one and a half times (about 540°) before diverging to a header. Advantageously, the plurality of coaxial coils are arranged in a tapered configuration to correspond to the taper of the fiber bundles encased in the interior housing. An outer casing or housing surrounds the heat exchanger coils and includes longitudinally arranged headers surrounding the ends of the coils so that water flowing into an inlet header circulates through each of the individual coils around the internal periphery of the housing, and exits at an outlet header. The plurality of coils are inserted as a unit into the outer casing, and then potted in position to provide a sealed heat exchanger unit enclosed in the outer housing.

The encased fiber bundle is inserted inside of the heat exchanger coils in the outer casing, with the interior housing cooperating with the outer casing to enclose the heat exchanger coils in an enclosed annular space defining a fluid flow path through the heat exchanger. The interior housing is sealed to the outer casing at the top and bottom ends in order to define appropriate flow paths through the heat exchanger and fiber bundle. Top and bottom caps are then applied to define appropriate gas manifolds or gas flow paths communicating with the inside of the hollow fibers in the fiber bundle.

In operation, water passes through the heat exchanger to adjust the temperature on the coils. Blood is introduced through the bottom of the outer casing at the bottom of the heat exchanger and flows upwardly over a plurality of the heat exchanger coils, into the apertures at the larger end, or top of the interior housing, and then downwardly over the hollow fibers for the transfer of blood gasses. The oxygenated blood then passes through the openings at the bottom or small end of the central core and out a bottom arterial blood outlet. Oxygen gas is passed through the top cap and gas manifold, through the hollow fibers to oxygenate the blood and remove carbon dioxide, and the out the bottom cap and gas manifold.

In one embodiment of this invention, the oxygenator contains an enclosed fiber bundle unit comprising a bundle of hollow fibers open on their ends for ducting gas therethrough with a casing around the fiber bundle. The casing is tapered at a predetermined angle. A fluid inlet and a fluid outlet are provided on the casing for ducting fluid around the outside of the fibers.

The oxygenator also contains a heat exchanger unit comprising a stack of tubular, coaxial coils defining an inner cavity tapered at the predetermined angle and corresponding in size to the exterior of the casing. The bundle unit is concentrically positioned within this cavity and compressed against the coils. The bundle unit cooperates with the heat exchanger unit to define a fluid flow path around the outside of the coils. The heat exchanger unit also has fluid inlet and a fluid outlet for ducting fluid through the inside of the coils.

The oxygenator further contains cap means cooperating with the heat exchanger unit to define gas passages which provide gas to the hollow fibers and remove gas from the fibers. The predetermined taper angle is advantageously about 2°, but may be up to about 6°.

In further variations, the oxygenator has a seal on one end of said fiber bundle unit for sealing against the heat exchanger unit, and a resiliently mounted seal on the opposite end of the fiber bundle unit to seal against the heat exchanger unit and to facilitate concentric positioning of the fiber bundle unit and the heat exchanger unit.

Another way of viewing the oxygenator of this invention, is by the construction of the flow paths through the oxygenator. There is one flow path through the inside of a plurality of fibers in the fiber bundle, a second liquid flow path around the outside of said fibers and around the coils of the heat exchanger, and a third flow path through the heat exchanger.

In this flow path embodiment, there is a housing around the bundle of fibers, sealed at opposite ends of the housing to define the gas flow path through the inside of the fibers. There is also a fluid inlet at one end, and a fluid outlet at the other end of the housing for ducting fluid through the inside of the housing around the outside of the individual fibers to define a portion of a liquid flow path. The heat exchanger unit comprises a stack of tubular, coaxial coils defining an inner cavity corresponding in size to the exterior of the housing. The bundle unit is concentrically positioned within that cavity and cooperates with the heat exchanger unit to define a portion of the liquid flow path around the outside of the coils. That liquid flow path further communicates with the fluid inlet in the housing. An outer casing enclosing the outside of the stack of coaxial coils also defines the flow path around the coils.

There is a fluid inlet and a fluid outlet for ducting heat exchange fluid through the inside of the coils to define the heat exchange fluid flow path through the inside of the coils.

The said gas flow path may further comprise a cap cooperating with the heat exchanger unit to define gas passages which provide gas to one end of the fibers and remove gas from the other end of the fibers. When the fiber bundle unit and said the exchanger unit are sealed at opposite ends, the gas cap provides a second, gastight barrier which prevents any liquid leaked across the housing seals from entering the gas path before the gas path passes through the fiber bundle.

In a further variation of this embodiment, the outer casing cooperates with the housing around the fiber bundle to form a cavity above the location at which the liquid flow path around the heat exchanger coils communicates with the liquid inlet in the housing. This cavity acts to collect gas escaping from the liquid flow path.

In a further variation of this invention, a fluid reservoir is provided which is in fluid communication with the liquid flow path through the oxygenator. Adaptor means on the oxygenator for allow the reservoir to be removably fastened to the oxygenator.

In a further embodiment of this invention, the fluid outlet on the housing has a tube communicating with the bottom portion of the bundle of fibers. A plurality of apertures in the tube open to the bundle to further define the liquid flow path to the inside of said tube. A bottom cap on the heat exchanger unit encloses the end of the fiber bundle unit through which gas exits to define a portion of the gas flow path. A conduit extending from the bottom cap to one end of the tube further defines a portion of the liquid flow path. The conduit is sealed to the tube to separate the gas path from the liquid flow path.

A sampling liquid flow path may also be added which comprises a passage communicating liquid from the inside of the tube to a port on the top of the oxygenator. The port is externally accessible to allow sampling of liquid after the liquid has passed through the fiber bundle.

In a still further embodiment of this invention, the heat exchanger unit used in the illustrated embodiment comprises a plurality of individual, tubular, coaxial coils each of which has an inlet end and an outlet end. The coils are stacked coaxially to define an inner cavity corresponding in size to the exterior of said casing. The fiber bundle unit is concentrically positioned within this cavity and cooperates with the heat exchanger unit to define a fluid flow path around the outside of the coils. A positioning member connects with the ends of the plurality of coils to maintain the coils in the coaxial stack.

In the illustrated embodiment of the heat exchanger, the coils encircle the cavity one and one half turns, with the inlet and outlet ends extending tangentially in the same direction from opposite sides of the coils. A spacer strip connects with a number of the tangential end portions of the coils, with the spacer strip having a plurality of apertures through which the ends of the coils extend. A spacer assembly is also provided, which comprises a pair of generally vertically orientated spacer strips. The spacer strips have a plurality of notches or apertures with each aperture being sized to receive at least a portion of one of the coils. A plurality of substantially parallel spacer bars connect the spacer members. The spacer bars are curved around the periphery of the cavity, positioned between two adjacent coils, and substantially coaxial with the coils.

The oxygenator of this invention is also constructed such that testing of components is more easily achieved. Thus, another embodiment of this invention comprises a bundle of hollow fibers open on their ends for ducting gas therethrough. A housing is placed around the bundle, with one end open. A stack of tubular, coaxial heat exchange coils surround the housing. A casing encloses the coils, with the casing having an open end surrounding the open end of the housing. The casing and the housing forming an annular passage therebetween. The housing further has a plurality of apertures for fluid communication between the annular passage and the spaces between the tubes. The ends of the bundle of tubes is sealed between adjacent tubes so that a liquid flow path is formed through the annular passage and through the bundle in the spaces between the tubes.

A ring-shaped cover fits onto and is sealed with the casing and the housing to close the end of said annular passage. A gas cap is placed radially within the cover and encloses the end of the housing. The cover and the cap are separate components so that the flow path may be pressure tested with the cover in place while the cap is not yet installed and while the ends of the fibers are accessible for the sealing of leaks in said fibers.

These and other advantages of the invention will be better understood with respect to the drawings, a brief description of which is provided as follows, and in which like numbers refer to like parts throughout.

BRIEF DESCRIPTION OF THE DRAWINGS

FIG. 1 is an elevated perspective view of the oxygenator/heat exchanger of this invention;

FIG. 2 is a lower perspective view at an angle opposite to that used in FIG. 1 of the oxygenator/heat exchanger of this invention;

FIG. 3 is an exploded perspective view of the oxygenator/heat exchanger of this invention;

FIG. 4a is an exploded perspective view of a portion of the heat exchanger assembly of this invention;

FIG. 4b is an exploded perspective view of a portion of the spacer assembly for the heat exchanger coils of this invention;

FIG. 5 is a partially sectioned, perspective view of the oxygenator/heat exchanger of this invention;

FIG. 6 is a partial cross-sectional view taken along 6—6, as shown in FIG. 5;

FIG. 7 is a perspective view of a microporous tubular fiber as used in this invention;

FIG. 8 is a cross-sectional elevation view of the oxygenator/heat exchanger of this invention;

FIG. 9 is a partially sectioned, exploded perspective view of an encased fiber bundle as used in this invention;

FIG. 10 is an exploded perspective view of the enclosed heat exchanger unit of this invention;

DETAILED DESCRIPTION OF THE PREFERRED EMBODIMENT

Figure 11:
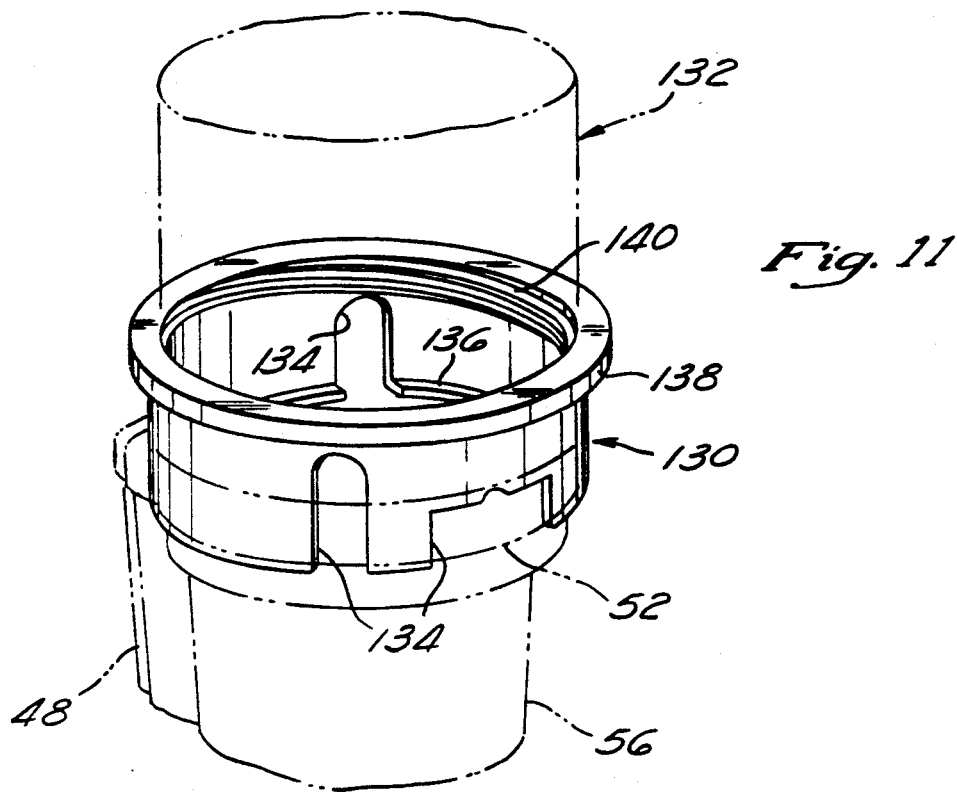
FIG. 11 is a partially sectioned perspective view of a venous adaptor for use with this invention.
Figure 12:
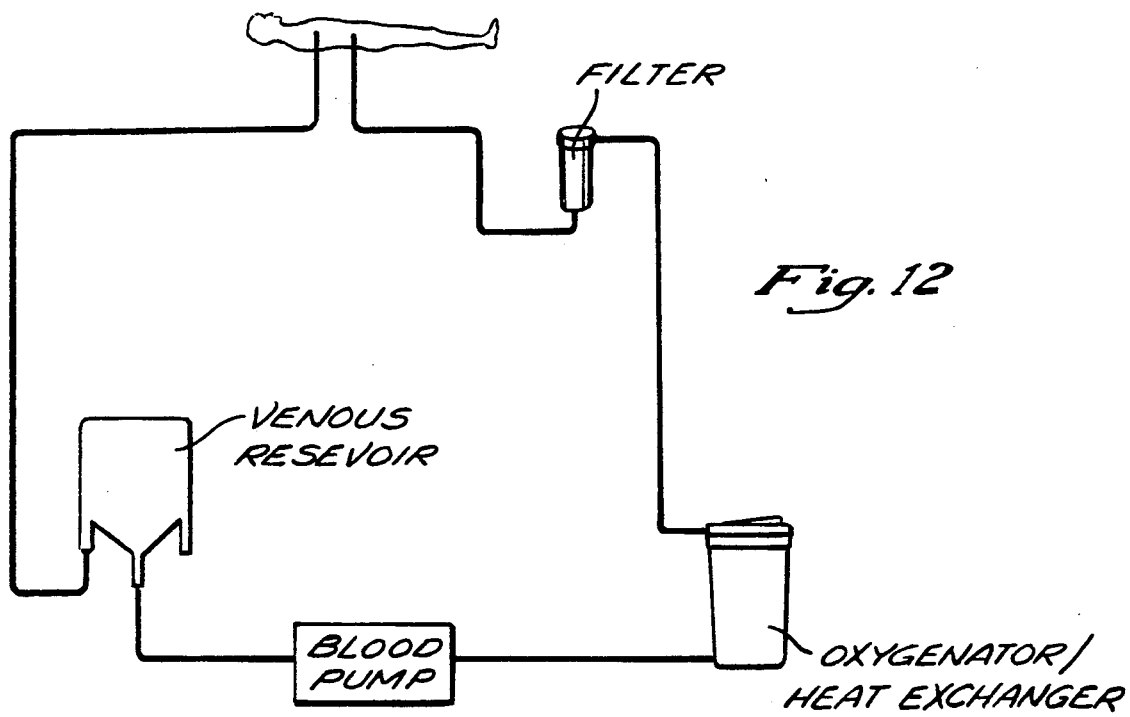
FIG. 12 is a schematic depiction of a blood oxygenator and heat exchanger as used during surgery.

Referring to FIGS. 1 and 5, but primarily to FIG. 5, there is shown the blood oxygenator/heat exchanger 12 of this invention, referred to hereinafter collectively as "oxygenator 12." The basic operation of the oxygenator 12 will be briefly described before explaining the details of the construction and operation. A fluid, such as venous blood, which is depleted in oxygen and rich in carbon dioxide, is introduced to the bottom of the oxygenator 12 at venous inlet port 14. As used herein, the "top" and "bottom" refer to upper and lower portions as viewed in the drawings.

The blood flows upward under pressure around a plurality of heat exchanger coils 16. At the top of the oxygenator 12 the blood passes through a plurality of apertures 18 in interior housing 20. The blood flows downward under pressure through a fiber bundle 22 during which the blood is re-oxygenated and the carbon dioxide is removed. At the bottom, or small end of the fiber bundle 22, the blood passes through a plurality of apertures 24 in a tapered centered core 26. From there the oxygenated blood exits through a tube 28 which connects the bottom or small end of the tapered center core 26 to an arterial port 30.

The oxygen used to replenish the venous blood is introduced into a top cap 32 through a gas inlet port 34. The top cap 32 forms part of a gas manifold communicating with the top 36 of the fiber bundle 22. Referring to FIG. 5, the gas enters the top 36 of the fiber bundle 22, passes through the length of the hollow fibers in the bundle 22, and exits the bottom or small end 38 of the fiber bundles. A bottom cap 40 forms a cavity or manifold communicating with the bottom 38 of fiber bundle 22. Gas is allowed to exit through gas vent 42 (FIGS. 1 and 5).

Referring to FIGS. 1 and 5, the temperature is controlled by passing a temperature controlled fluid through the heat exchanger coils 16. The fluid, preferably water, is introduced through an inlet port 44, which communicates with a manifold or first header 46 which is in fluid communication with one end of each of the plurality of heat exchanger coils 16. The fluid passes through the heat exchanger coils 16, and exits at a second header 48 (FIG. 1) which is in fluid communication with the remaining ends of the heat exchanger coils 16. A fluid outlet port 50 (FIG. 1) allows the fluid to be removed from the header 48.

A plurality of fluid communication ports and a sampling port are also provided in the oxygenator 12 as will be subsequently described.

As illustrated in FIG. 3, the oxygenator 12 is assembled by combining several subassemblies and parts into a completed unit. Briefly described, these subassemblies and parts comprise the top cap 32, an outer casing cap 52, an enclosed fiber bundle unit 54, an enclosed heat exchanger unit 56, and the bottom cap 40. The enclosed fiber bundle unit 54 will be described first.

Referring to FIGS. 3 and 5, but primarily to FIG. 5, there is a tapered central core 58 having a generally tubular, but tapered, exterior shape such that its top end 60 is larger than its bottom end 62. Another way of describing the tapered central core 58 is that it has a frusto-conical shape. The taper on the central core 58 is about 2°. Adjacent the smaller, or bottom end 62 of the core 58 are located the plurality of apertures 24 which extend through the thickness of the core 58. Between the apertures 24 and the larger top end 60, is located a plug 64 which substantially blocks the interior of central core 58. A plurality of openings or slots 25 (FIG. 5) are located on the exterior portion of the central core 58 such that they have one end communicating with the apertures 24. The slots 25 extend only part way through the wall of the central core 58. A portion of the inside of the core 58, adjacent the smaller or bottom end 62 and apertures 24 is cylindrical in shape.

In the illustrated embodiment, at the center of the plug 64 is located a nipple 66 extending towards the larger top end 60 of core 58. A flexible tube 68 is in fluid communication with the nipple 66 that extends towards the larger top end 60. A one way valve 69 is attached to the tube 68.

A plurality of hollow, microporous fibers are wound onto the uniformly tapered outside of central core 58. A portion of one such hollow tube 70 is illustrated larger than actual size in FIG. 7. The tubes 70 comprise microporous or semi-permeable membranes in a hollow, tubular configuration. A microporous polypropylene hollow fiber membrane, having a diameter of 400 microns, and a wall thickness of about 25 microns, is believed to be suitable for use.

Referring again to FIG. 5, a plurality of the fibers, or tubular membranes 70 (FIG. 7) are wound onto the central core 58. It is believed suitable to wind the membranes 70 in bands of 18 fibers with the orientation of the successive layers of the windings being varied. A total of abut two (2) square meters of surface area is believed suitable for an oxygenator used with an adult patient. The means of winding such membranes 70 onto tubular cores is the subject of a number of patents, and a number of methods are known in the art which could achieve such a winding.

The top and bottom ends 72 and 74 of the fiber bundle 22, as viewed in FIG. 5, respectively, are sealed to provide a gastight seal among the outside of the plurality of fibers 70 (FIG. 7). Typically a potting compound such as urethane is applied to the outside of the fibers and allowed to cure. The bundle of fibers is then cut across the potting compound to expose the ends of the plurality of tubes. Thus, gas can flow through the length of the tubes, but cannot flow through the sealed ends 72 and 74 of the fiber bundle. To the extent the potting compound does not seal the fiber bundle 22 to the ends of the inner core 58, an additional sealant may be provided to ensure a gastight seal.

The fiber bundle 22 is wound onto the tapered core 58 with a substantially uniform thickness such that the outer circular periphery of the bundle 22 has substantially the same amount of taper as the central core 58. The central core 58 and fiber bundle 22 are then enclosed or encased by interior housing 20.

Referring to FIGS. 3 and 5, the interior housing 20 has a frusto-conical shape, comprising a tubular, tapered housing with a length substantially equal to the length of the central core 58. The degree of taper is also substantially the same as the inner core 58. Adjacent the larger, top end of the interior housing 20, as viewed in FIGS. 3 and 5, there are located the plurality of apertures 18, which extend through the thickness of the casing 20. The apertures 18 are above a flange or lip 76 extending radially outward from the interior housing 20, and a flange 78 having a generally "L-shaped" cross-section which extends outward and upward from the interior housing 20.

An O-ring 79 is located in a recess (not shown) on the upward extending portion of the L-shaped flange 78. The flange 78 thus acts as a spring to resiliently urge the O-ring 79 outward against any radially compressive force or contacting structure. Adjacent the smaller, or bottom end of the interior housing 20 is another O-ring 77 located in a recess (not shown).

The diameter of interior housing 20 is such that, when it is positioned concentrically with the central core 58, with the corresponding ends being radially aligned, the interior housing 20 is slightly smaller in diameter than the corresponding diameter on the outside of fiber bundle 22. The assembly procedure is thus to slide the interior housing 20 over the core 58 and fiber bundle 22 as far as the interior housing 20 will go. At that point, the interior housing 20 is pushed further until the ends of the casing 20 are positioned radially outward of the ends 60, 62 of the central core 58. This final positioning causes some slight radial compression in the fiber bundle 22, but provides a close fit with the casing. In the illustrated embodiment, the fiber bundle 22 is wound around the center core 58, and the casing 20 is positioned before the potting compound is cut at each end of the enclosed fiber bundle unit 54. To ensure a gastight seal, a sealant may be applied between the ends of the interior housing 20 and the mating ends 72, 74 of fiber bundle 22.

When the bundle 22 and casing 20 are assembled, the apertures 18 in the interior housing 20 are located below the potted area at the larger, top end 72 of the bundle 22. Thus, the apertures 18 provide a fluid communication means to the fiber bundle 22 which is encased between the central core 58 and interior housing 20, and sealed on opposite ends by potting compound.

The apertures 24 and slots 25 in central core 58 are located above the potted area on the end 74 of the fiber bundle 22. The slots 25 act to provide a hole through the tubular wall of core 58 with the size of the opening to the hole being larger on one side of the wall than on the other side. As shown, the wall defining a portion of the fluid flow path around the outside of the fibers has a plurality of apertures configured to have a larger opening adjacent the fibers and a smaller opening on the opposite side of the wall.

The slots 25 effectively increase the contact area or drainage area of the apertures 24 with the fiber bundle 22 since blood flows into the slots 25 which in turn channels the blood into the apertures 24. Thus, a larger drainage area and reduced resistance to fluid flow is provided while minimizing the size of the apertures 24.

The apertures 24 provide a fluid communication means from the fiber bundle 22 to the inside, bottom (smaller) end of the central core 58. There is thus provided an enclosed fiber bundle having a first flow path through the inside of the fibers and a second flow path around the outside of the fibers.

The fit between the outside of the fiber bundle 22 and the adjacent interior housing 20 should be as close as possible in order to prevent blood from shunting through any gap between the fiber bundle and the housing. Currently, the outer diameter of cylindrical fiber bundles must be closely controlled, and the diameter of the containers into which they fit are also closely controlled; even then, a slight gap sometimes occurs. The use of a tapered core and casing to enclose a tapered fiber bundle allows for a wider variation in the manufacture of the fiber bundle 22 while still insuring a tight fit. There is thus advantageously provided not only a less expensive means of manufacture, but a less expensive means of assembly. Moreover, the assembly is less likely to damage the fibers on the outside of the bundle than prior devices and assembly techniques. There is also advantageously provided an enclosed subassembly of fiber bundles which can be shipped and handled during assembly with much less chance of damaging the tubular fibers.

The enclosed heat exchanger unit 56 (FIGS. 3 and 10) will be described next. Referring to FIG. 10, broadly described, the heat exchanger unit 56 comprises an outer casing cap 52, an outer casing 92, a plurality of coils 16 together with a spacer assembly 84 and spacer strips 85.

Referring to FIGS. 4, 5, 6, 8 and 10, but primarily to FIG. 5, a plurality of individual heat exchange coils 16 are assembled in a tapered, coaxial configuration. Preferably, the heat exchanger coils 16 comprise anodized aluminum coils. Spiral ribs are formed on the curved portions of the heat exchanger coils 16 by means known in the art and not described in detail herein. Each of the coils 16 has an input end 80 (FIGS. 4 and 5) and an outlet end 82 for the inlet and outlet of a heat controlled fluid, respectively.

The coils 16 are shaped such that they would wrap around a frusto-conical shape having a diameter and taper corresponding to the diameter and taper of the tapered interior housing 20. Thus, the coils 16 are wrapped about a circle with the coils 16 adjacent the top or larger end of the oxygenator (when installed) being wrapped around a larger circle than those at the bottom, narrower end of the oxygenator (when assembled). Alternately phrased, the coils 16 are coaxially positioned to define a tapered cavity.

The ends 80, 82 extend at a tangent to the circle and to the coaxial assembly of coils, in the same direction and from opposite sides of the circle and coaxial assembly of coils. Each of the coils 16 wraps one and one-half times (approximately 540°) about this circular shape. Advantageously, thirteen individual coils 16, each with ends 80, 82, can be stacked coaxially, positioned by spacer assembly 84 and spacer members 85. The ends 80, 82 of the stack of coils will form two lines, having a slight "V" shape because of the taper of the stack of coils.

Referring to FIGS. 8 and 10, a pair of spacer strips 85 are shown which comprise a longitudinal member having a rectangular cross-section. A plurality of circular holes are formed in the spacer strips 85 to correspond to the size and location of the ends 80, 82 of the coils 16. The ends 80, 82 of the coils 16 are inserted through the holes in the spacer strips 85 with the strips 85 holding the coils 16 in position. The spacer strips 85 have a length approximately equal to the longitudinal length of headers 46, 48. After the plurality of coils 16 are assembled in a coaxial configuration, the assembly is joined to a spacer assembly 84.

The spacer assembly 84 as best illustrated in FIG. 4a, and comprises two spaced apart longitudinal spacer members 86. Each of the members 86 have a plurality of cylindrical notches 88 on the side facing away from the other member 86. The ends 80, 82 of the coils 16 fit into the plurality of notches 88. A plurality of substantially parallel, curved spacer bars 90 extend between and join the members 86. The spacer bars 90 occupy substantially the same position as the missing half loop on the one and one-half turn coils 16. The spacer bars 90 serve to displace volume so the total volume of priming fluid is lower, and also prevent shunting of the fluid which might reduce contact with the heat exchange coils 16.

The spacer assembly 84 is inserted into the plurality of coaxial coils 16 held by the spacer strips 85, with that combined assembly then being inserted into an outer housing or casing 92, as illustrated schematically in FIG. 10. The outer casing 92 is best described with reference to FIGS. 1 and 5. The outer casing 92 comprises a generally hollow, frusto-conical shape which has a middle portion 96 which has an inside tapered at an angle corresponding to the taper on the enclosed fiber bundle unit 54 (FIG. 3).

Extending tangentially from opposite sides of the outer casing 92 are two longitudinal headers 46, 48 which open into the inside of the outer casing 92. The headers 46, 48 extend for a substantial portion of the axial length of the outer casing 92 and are shown as extending in the same direction. The headers 46, 48 form a slight "V" shape because of the taper of the outer casing 92 from which they extend. The headers 46, 48 are substantially rectangular in cross-section. Referring additionally to FIG. 8, the headers 46, 48 contain a space sufficiently large to enclose the ends 80, 82 of the plurality of heat exchanger coils 16. An enlarged area 93 extends longitudinally along the length of headers 46, 48. The enlarged area 93 comprises a localized increase in the space between the opposing sides of headers 46, 48, extending the length of headers 46, 48.

Referring now to FIGS. 1, 2, and 5, there are several stepped changes in the diameter of the outer casing 92. A bottom portion 94 has the smallest diameter and extends axially for a distance of about 1.5 inches. The bottom portion 94 tapers axially at about ½°, with the bottom end being smaller than the top end. The bottom, or free end of bottom portion 94 terminates in a bottom lip 95 which extends radially inward. A plurality of slots 97 are formed in the bottom lip 95 to accommodate the attachment of bottom cap 40 as described later. The bottom portion 94 can be made of a uniform diameter, without a taper.

The middle portion 96 has a slightly larger diameter than that of bottom portion 94, and as mentioned above, tapers at an angle corresponding to that of the encased fiber bundle unit 54. The small end of the middle portion 96 joins the large end of the bottom portion 94. The axial length of the middle portion 96 corresponds to substantially the axial length of the plurality of coils 16 on the spacer assembly 84.

A top portion 98, seen best in FIG. 3, has a larger diameter than the middle portion 96, and is tapered at about ½°. The smallest diameter end of the top portion 98 joins the largest diameter end of the middle portion 96.

The headers 46, 48 extend from the upper part of the bottom portion 94, through the middle portion 96, and through the top portion 98. The headers 46, 48 are integrally molded with the outer casing 92.

Adjacent the juncture of the bottom portion 94 and the middle portion 96, on the side of the casing 92 opposite the headers 46, 48, are located two access ports, the venous inlet port 14, and a venous temperature access port 100 (FIG. 2). These types of ports are known in the art and are not described in detail herein. As previously mentioned, ports 44, 50 are also formed in the upper portion of the headers 46, 48, respectively (FIG. 1).

Referring to FIGS. 5, 8, and 10, the assembly of the enclosed heat exchanger unit 56 will be described. The combined assembly of the heat exchanger coils 16, spacer strips 85 and spacer member 86 is oriented so that the ends 80, 82 correspond to the location of headers 46, 48, respectively, and the location of the spacer strips 85 corresponds to the location of the enlarged areas 93. The assembly of the coils 16, the spacer member 86, and the spacer strips 85 are then inserted within outer casing 92. The diameter and taper of the middle portion 96 of outer casing 92 corresponds to the configuration of the assembly of coils 16 and spacer members 86 to form a substantially close fit. The larger end, or top of the plurality of coils 16 is at or adjacent to the beginning of the top portion 98 when the coils 16 are placed inside the outer casing 92.

Referring to FIGS. 5 and 6, when assembled, the coaxial coils 16 are located between the interior casing 20 and the outer casing 92. The ribs on the coils 16 spiral around the coils 16 to create a non-uniform diameter, which effectively prevents a fluid tight seal from forming when the casings 20 and 92 are pressed against the coils 16. Thus, the ribs on the coils serve to insure a fluid flow path across the coils 16 exists between the casings 20 and 92.

Referring to FIG. 8, the spacer members 86 abut against the outer casing 92 when the plurality of coaxial coils 16 are inserted. Preferably, the edges of the spacer members 86 are configured to coincide with the interior shape of the outer casing 92 so as to form a close fit. The spacer strips 85 are sized so they abut the inside of the enlarged areas 93 in the headers 46, 48.

The enclosed heat exchanger unit 56 is completed by attaching the outer casing cap 52 and sealing the unit to define flow passages for the fluid flow through the heat exchanger coils 16.

Referring to FIGS. 3 and 5, the outer periphery of casing cap 52 is configured to correspond to the top of the outer casing 92. The outer casing cap 52 has a generally circular outer shape with two tabs 106 extending tangentially, in the same direction, but from opposite sides of the periphery of cap 52. The tabs 106 are configured to correspond to the outside peripheral shape of the ends of headers 46, 48 as they connect to the outer casing 92. The tabs 106 fit over the headers 46, 48 as the cap 52 is placed over the top of the outer casing 92.

The cap 52 has a downwardly depending flange 109 which forms a circular hole or aperture 108 in the center of the cap 52 (FIG. 3). There are a plurality of bayonet apertures 113 (FIG. 3) formed in the flange 109. The flange 109 is substantially cylindrical in shape, having a diameter approximating that of the L-shaped flange 78 on the interior housing 20.

The outer periphery of the outer casing cap 52 also has a depending flange 110 (FIG. 5) substantially parallel to the longitudinal axis of aperture 108. The flange 110 corresponds to the shape of the outer periphery of cap 52, including the shape of the tabs 106. Spaced slightly inward from the flange 110, is a second locking flange 111 (FIG. 5) which depends substantially parallel to, but spaced from flange 110. On the side of the cap 52 opposite the tabs 106, is located a venous gas port 112.

Referring to FIG. 5, it can be seen that the flanges 110, 111 are located so that the top portion of outer casing 92 fits between the flanges in a sealing manner. Moreover, the tabs 52 fit closely over the outside of the top of the headers 46, 48. Advantageously, a sealing adhesive can be provided along the periphery of the top portion 98, or between the flanges 110, 111, in order to ensure a gastight seal.

After insertion of the cap 52 onto the top of the outer casing 92, a potting material 102 is inserted into the headers 46, 48 so that a portion of the ends 80, 82, spacer strips 85, the spacer members 86 are sealed to the outer casing 92 in a gastight manner. The spacer strips 85 are sealed into the enlarged areas 93 by injecting a potting material 102, such as a thixotropic urethane, into the enlarged area 93 so that both sides of the spacer strips 85 are sealed to the headers 46, 48, while the ends of the coils 80, 82 are left open for the flow of fluid through the coils 16. The spacer strips 85 are sized to fight closely within the enlarged area 93 so as to provide a semi-seal which helps control the flow of the potting compound 102 around the strips 85. The spacer strips 85 can be potted in position before the outer casing cap 52 is sealed in place.

Spacer assembly 84 is also sealed to the inside of the outer casing 92 adjacent the juncture of headers 46, 48 with the outer casing 92. The spacer assembly 84 is sized to fit close to the corresponding portions of the inside of casing 92 to provide a semi-seal which helps control the flow of potting compound 102. The casing 92 can be positioned horizontally to help control and direct the flow of the potting compound 102. The introduction of the potting material can be achieved through apertures formed in the casing 92 (not shown), which apertures are sealed by the potting compound 102. The potting material is applied in a manner such that it does not cover the apertures in the ends 80, 82 which allow a heat exchanger fluid to pass through the coils 16.

The enclosed heat exchanger unit 56 (FIG. 3) provides a separately assembled subassembly which allows movement and handling of a heat exchanger while minimizing damage to the heat exchanger coils. The use of the manifolds or headers 46, 48 allows a fluid of substantially uniform temperature to be introduced into the inlet ends 80 of the plurality of coils 16, and allows uniform exit of the fluid from the coils 16 through the exit header 48. The mixing chamber effect of headers 46, 48 prevents any hot spots from occurring throughout any single heat exchanger coil 16. The separate assembly of the heat exchanger unit also allows separate testing for leakage of the temperature control fluid before final assembly of the oxygenator 12.

Referring to FIGS. 1, 3 and 5, the top cap 32 comprises a generally circular cap having a substantially flat portion with a depending lip 114 around its outer periphery. At the upper portion of the top cap 32 are located a plurality of bayonet mounting tabs 116 which comprise radially extending projections located at several points around the periphery of the top cap 32. The spacing of the bayonet mounting tabs 116 is such that they correspond with the bayonet slots 113 in the outer casing cap 52. Located on the exterior surface of the top cap 32 is the gas inlet port 34 which communicates with the interior of the top cap 32.

Also located on the exterior surface of top cap 32 is an arterial sample port 118 which communicates with the interior of the top cap 32 and the tube 68 and one way valve 69 (FIG. 5). The sample port 118, via tube 68 and nipple 66, allows access to oxygenated blood as it exits the fiber bundle 22 through apertures 24.

Referring to FIGS. 2, 3 and 5, the bottom cap 40 comprises a generally flat disk having a plurality of L-shaped mounting tabs 119 extending substantially perpendicular to the flat surface of cap 40, with an exterior portion of the tabs 119 extending radially outward thereof. The tabs 119 are located on the cap 40 to correspond with the location of slots 97 in bottom lip 95 of the outer casing 92.

At the center of the cap 40 is located the flow tube 28 which comprises a substantially hollow cylinder extending upward from the bottom cap 40. Adjacent the outermost end of the tube 28 are located two O-rings 120 which are seated in a rectangular shaped aperture (not shown) in the tube 28. The diameter of the O-rings 120 and the adjacent portion of the tube 28 corresponds to the diameter of the smaller, or bottom end 62 of the tapered center core 26 (FIG. 5).

A plurality of tubes are in fluid communication with the end of the tube 28. Thus, the aperture port 30 is in fluid communication with the tube 28 and extends radially outward from the tube 28 and the bottom cap 40. Oriented about 180° opposite to the port 30 is an arterial temperature port 122. Located at about 90° to the port 30, is an arterial recirculation port 124, which is in fluid communication with the center of the tube 28.

Referring to FIGS. 3 and 5, the assembly of the oxygenator 12 will now be described. Two subassemblies are separately assembled as previously described, the enclosed fiber bundle unit 54, and the enclosed heat exchanger unit 56. The enclosed fiber bundle unit 54 is then inserted through the aperture 108 in the outer casing cap of the enclosed heat exchanger unit 56. The taper on the interior housing 20 and the interior portion of coils 16 are substantially the same and oriented in the same direction. Thus, the smaller end of the enclosed fiber bundle unit 54 can be readily inserted into the larger opening 108 in the enclosed heat exchanger unit 56.

The relative sizing of the components is such that the O-ring 77 on the smaller, or bottom of the interior housing 20 abuts the interior side of the bottom portion 94 of the outer casing 92 when the enclosed fiber bundle unit 54 is resting on the inside of the enclosed heat exchanger unit 56. Similarly, the O-ring 79 on flange 78 abuts the inside of the flange 109 on outer casing cap 52. Further, the coils 16 abut the outside diameter of interior housing 20. A force is then applied to the enclosed fiber bundle unit 54 to force the tapered parts into a tighter fit. Applying an 80-pound force by an air piston in contact with the larger, or top end of the enclosed fiber bundle unit 54 has been found suitable.

The coils 16 limit the fit between the enclosed fiber bundle unit 54 and the enclosed heat exchanger unit 56. After the parts are forced into this tight fit position, the heat exchanger coils 16 are in a substantially tight fit in the annular space defined between the walls of the outer casing 92 and the walls of the interior housing 20 along the length of the middle portion 96. The flange 76 on interior housing 20 (FIG. 4) helps limit the position of the enclosed fiber bundle unit 54 with respect to the enclosed heat exchanger unit 56 as the flange 76 would contact the coils 16 to limit relative motion between units 54 and 56. The flange 76 also insures the coils 16 are not positioned so as to block the apertures 78 which allow fluid flow into the enclosed fiber bundle 22.

The O-ring 77 provides a fluid-tight seal between the bottom of the interior housing 20 and the bottom portion 94 of the outside casing 92. The L-shaped flange 78 at the larger end, or top of the enclosed fiber bundle unit 54 is resiliently urged against the flange 109 on the end cap 52 of the enclosed heat exchanger unit 56. The O-ring 79 on flange 78 provides a seal between the top portions of the enclosed fiber bundle unit 54 and the enclosed heat exchanger unit 56.

To ensure that a gastight seal exists, beads of adhesive can be placed at appropriate points along any exposed and accessible interfaces between the enclosed fiber bundle unit 54 and the enclosed heat exchanger unit 56. Placing the adhesive adjacent the O-rings 77 and 79 is believed suitable.

The top and bottom caps 32, 40, respectively, are then attached and, if appropriate, sealed in place with an adhesive to ensure gastight joints. Specifically, the one-way valve 69 is connected to the port 118 in the top cap 32. The flange 114 on top cap 32 is then inserted into the aperture 108 on the outer casing cap 52. The bayonet tabs 116 correspond with the bayonet slots 113 to allow the insertion. After it is inserted, the cap 32 is rotated to lock the bayonet tabs 116 into position and prevent inadvertent removal of the top cap 32. Adhesive may be placed in the groove between flange 78 and the top portion of interior housing 20 to seal with the lip 114 on top cap 32. The top cap 32 defines a gas tight enclosure or gas manifold communicating with the top 36 of the fiber bundle 22.

The bottom cap 40 is inserted such that the O-rings 120 on tube 28 seal against the cylindrical portion on the inside of the center core 58. A bead of adhesive is advantageously placed between the O-rings 120 to insure a seal. The projections 119 fit in the slots 97 in the lower lip 95 of the outer casing 92. After insertion, a rotation of the bottom cap 40 positions the tabs 119 so they no longer coincide with the slots 97 and thereby inhibits inadvertent removal of the bottom cap 40.

The bottom cap 40 provides a gas enclosure or gas manifold communicating with the gas outlet end of the fiber bundle 22, namely the bottom end 38. For safety reasons, the bottom cap 40 is not completely sealed to the outer casing 92. Outlet port 42 channels gas away from this gas manifold.

The use of separate subassemblies for the heat exchanger unit and the blood oxygenator unit provides much simpler and quicker manufacturing and assembly than has previously been available. The use of the tapered fit on the major subassemblies allows the use of larger tolerances in manufacturing and accommodates errors in assembly which leads to a quicker and faster assembly while providing a good seal on the unit.

The illustrated design facilitates testing for leakage. The flow path of the heat exchanger fluid may be tested at the subassembly stage when the coils 16 are sealed in place to the casing 92, but more advantageously, after the outer casing cap 52 is glued in position and all of the potting material 102 is inserted and cured. If a leak is detected at this subassembly stage, appropriate steps may be taken without risk of damaging, or discarding the remainder of the oxygenator 12.

The use of two caps, the top cap 32 and outer casing cap 52, also allows access to the end 36 of the fiber bundle unit 22 to greatly facilitate testing of the fluid flow path and the gas flow path. Before the top cap 32 is sealed in place, water may be pumped through the oxygenator 12 to detect leaks. Specifically, water may flow, under operating pressure, across the heat exchange coils 16, through apertures 18, through the enclosed fiber bundle 22, and out apertures 24 in center core 58. If there is a leak in the fluid flow path, it may be detected and appropriate remedial steps, if any, taken. The pressurized water will also enter through any leak in the fiber bundle, and flow through the fiber tube until water appears on the ends 36, 38 of the fiber bundle 22. Thus, one test checks both the entire fluid flow path and the gas flow path through the fiber bundle 22.

The placement of the O-ring seals 77 and 79 (FIG. 4) between the enclosed fiber bundle assembly 54 and the enclosed heat exchanger assembly 56 also insures that a leak across the seals does not contaminate the oxygenating gas flow path. Any leak of fluid into the inside of the fibers in the fiber bundle 22 will degrade the oxygenation performance of the oxygenator 22. A leak across seal 79 may allow fluid to leak to the outside of the oxygenator 12, but the sealed lip 114 on top cap 32 prevents any fluid from entering the gas flow path into the inside of the fibers. A leak across seal 77 is into the post oxygenation portion of the gas flow path, in to an unsealed chamber so any fluid will not travel upstream against the flow of the gas into the fiber bundle. Thus, the seal design between the sub-assembled units 54 and 56 insures against fluid leakage into the oxygenating gas flow path.

The use of the resiliently mounted O-ring 77 on the larger end of the enclosed fiber bundle unit 54, allows the more rigidly mounted seal 77 to be seated by axially positioning the unit 54, while the resilient mounting of seal 78 accommodates that axial motion. Both seals 77 and 78 accommodate axial motion of the enclosed fiber bundle assembly 54. The resilient mounting of seal 77 thus allows for easier assembly of the unit, and allows a wider variability in manufacturing tolerances to be used.

The concentric arrangement of the heat exchanger coils 16 with the fiber bundle 22 allows a folding of the fluid flow path before oxygenation which in turn provides a location for placing a bubble trap to collect and remove bubbles from the fluid. The flange 76 is placed so as to direct the flow of fluid into the bottom of the bubble trap formed by the space between flanges 109, 111 on the outer casing cap 52 (FIG. 4).

The tube 68 communicates oxygenated blood from the bottom of the fiber bundle 22, through the inside of the oxygenator, to a port 118 which is easily accessible at the top of the oxygenator. The location of the arterial sample port 118 on the top of the oxygenator 12 provides a readily accessible means for the purfusionist to sample the oxygenated blood, without having to bend outwardly and grapple with the bottom of the unit. Moreover, the internal routing of the tube 68 prevents inadvertent damage to or pulling of the tube 68.

The space between the flanges 109, 111 on the inside of the top cap 32 is in fluid communication with the annular space containing the heating coils 16. Since the space between the flanges 109, 111 is positioned above the coils 16, and positioned above the apertures 18 through which the blood flows into the fiber bundle 22, the space between the flanges acts as a gas trap to capture any gas bubbles dissolving out of the blood flowing through the oxygenator 12. The venous port 112 is in fluid communication with this space between the flanges 109, 111, and it can be used to remove not only any excess gas, but to sample the blood at this point in the oxygenator 12.

The use of a concentrically positioned heat exchanger and blood oxygenator also allows a much smaller and more compact unit than previously available. The use of the concentric heating coil and blood oxygenator also provides some increase in the efficiency of the heat exchange unit in the sense that only the interior housing 20 separates the blood flowing around the fiber bundle 22 from the heat exchange coils 16. Thus additional heat transfer from the coils 16 can occur through the interior housing 20 to the blood in fiber bundle 22 in order to provide an increased efficiency of the heat exchanger.

The described arrangement of the heat exchanger coils 16 in conjunction with the concentric blood fiber bundle 22 also results in a low pressure drop in the blood oxygenator 12. Thus, an 11 psi static flow pump is believed suitable for use.

An oxygenator 12 suitable for use with an adult has an approximate surface area of the fibers 70 and the fiber bundle 22 of about 2 square meters. The priming volume is approximately 400 milliliters. The blood flow rate through such a unit can be varied between one and seven liters per minute, with a maximum gas flow rate of 15 liters per minute. The maximum water pressure through the heat exchange coils 16 is approximately 80 pounds per square inch for a one-half inch diameter inlet and outlet ports 44, 50, respectively. The various casing and cap components of the oxygenator can be made out of a clear polymer material such as polycarbonate, acrylic, ABS, SAN, etc.

The 2° taper described in the illustrated embodiment is believed suitable for use. While a slightly smaller taper may be suitable for use, the amount of taper should be greater than that normally used to ensure easy release during molding of the critical plastic injected part for blood oxygenators. For example, the mold release taper for a container in which a fiber bundle would be positioned is typically a maximum of ½° to 1°, with the goal being a zero degree taper. Prior practice was to attempt to obtain no taper at all because any gap between the fiber bundle and the container allows blood to shunt or bypass the fiber bundle by flowing through that gap. Thus, the present invention goes against conventional practice by placing a taper on parts which were previously designed and manufactured with the goal of eliminating any taper whatsoever.

On the other hand, too great of a taper angle on the parts will limit the amount of adjustability and tolerance variation which can be accommodated when fitting the enclosed fiber bundle unit 54 into the enclosed heat exchanger unit 56. As the taper angle increases, less axial motion of the respective parts is required in order to create the same amount of interference fit between the parts. Thus, while greater tapers may be possible, a taper angle of about 2°–6° is believed desirable, and 2°–4° is believed even more advantageous for the taper on such components as the interior housing 20, the fiber bundle 22, and the assembly of coaxial coils 16.

In a further embodiment of this invention shown in FIG. 11, an adapter 130 is used to removably attach a venous reservoir 132. The adapter 130 comprises a generally tubular cylindrical structure having an inner diameter sized to fit over the outside diameter of the circular portions of outer casing cap 52. There are a plurality of slots 134 in the bottom portion of the adapter 130 which are located to coincide with the location of any components which extend radially outward of the outer periphery of the outer casing cap 52. Such projections would include the tabs 106 and the ports 34 and 118.

There is a flange 136 extending radially inward of the adapter 130 and located such that when the adapter 130 is positioned on the oxygenator 12, the flange 130 abuts against a portion of the outer casing cap 52 in order to position it and stabilize the adapter 130.

At the top end of the adapter 130 is a flange 138 which extends radially outward from the center of the adapter 130. A screw thread 140 is formed in the top of the adapter 130 on the inside of the cylinder. The venous reservoir 132 (shown schematically) has a corresponding set of external threads (not shown) which allow the venous reservoir 132 to be removably engaged with the adapter 130.

The adapter 130 allows the venous reservoir 132 to be removably attached to the blood oxygenator 12. The venous reservoir 132 is used to hold sufficiently large volumes of blood to handle normal fluctuations in flow returning from the patient. The adapter 130 allows a single venous reservoir to be used before, during, and after surgery, without having to replace the venous reservoir or disconnect and reconnect a plurality of connecting tubes.

While certain features of this invention have been described in detail with respect to various embodiments thereof, it will of course be apparent that other modifications can be made within the spirit and scope of this invention.

We claim:

1. A hollow fiber oxygenator comprising
   an enclosed fiber bundle unit comprising:
   a bundle of hollow fibers open at the ends thereof for ducting gas therethrough, said bundle exterior being tapered at a predetermined angle;
   a casing around said fiber bundle, said casing being tapered at approximately said predetermined angle, said bundle and said casing being dimensioned and positioned such that said bundle has been axially inserted into the casing sufficiently far to create an interference fit between the exterior of the bundle and the interior of the casing, which results in readily compressing said bundle; and
   means defining a fluid inlet and means defining a fluid outlet in said casing for ducting fluid through spaces between said hollow fibers;
   a heat exchanger unit comprising;
   a plurality of tubular, coaxial coils stacked along a common axis defining an inner cavity tapered approximately at said predetermined angle and corresponding in size to the exterior of said casing, said bundle unit being concentrically positioned with said cavity creating a tight fit between said casing and said coils, said bundle unit cooperating with said heat exchanger unit to define a fluid flow path around said coils;
   means defining a fluid inlet and means defining a fluid outlet for ducting fluid through said coils;
   cap means cooperating with said heat exchanger unit to define gas passages which provide gas to the interior of said hollow fibers and remove gas from said hollow fibers;
   means communicating with said fluid outlet in said casing communicating fluid away from said oxygenator;
   said casing fluid inlet being near the top of the bundle unit and said casing fluid outlet being near the bottom of said bundle unit and opening to a center core in the bundle unit; and further comprising:
   an internally located tue communicating fluid from adjacent the bottom of said fiber bundle center core to means defining a port on the top of said oxygenator to allow sampling of fluid which has passed through said fiber bundle.

2. An oxygenator as defined in claim 1, further comprising:
   a seal on an end of said fiber bundle unit for sealing said fiber bundle unit to said heat exchanger unit; and
   resiliently mounted sealing means on an opposite end of said fiber bundle unit to seal said fiber bundle unit to said heat exchanger unit and to facilitate concentric positioning of said fiber bundle unit and said heat exchanger unit.

3. An oxygenator as defined in claim 1, wherein said predetermined angle of taper is about 2°.

4. An oxygenator as defined in claim 1, wherein said predetermined angle of taper is between about 2° to 4°.

5. An oxygenator as defined in claim 1, wherein said predetermined angle of taper is between about 2° to 6°.

6. An oxygenator as defined in claim 1, further comprising:
   a fluid reservoir in fluid communication with said oxygenator; and
   adaptor means on said oxygenator for removably fastening said fluid reservoir to said oxygenator.

7. An oxygenator as defined in claim 1, wherein said heat exchanger coils are separate coils, each of which encircles said fiber bundle one and one-half times, and wherein at least one end of each of said coils terminates in a header providing a mixing chamber for at least the fluid entering the coils.

8. A hollow fiber oxygenator, comprising:
   a fluid tight outer casing having a fluid communication port at the bottom end of the casing, and a pair of fluid headers with the fluid ports in communication with said headers;
   a plurality of separate, heat exchanging coils stacked coaxially along a common axis within said casing and having input and output ends which terminate in said fluid headers so that fluid can be circulated through said coils to very the temperature of the coils, said stacked coils defining an inner cavity tapered at a predetermined angle;
   an encased fiber bundle concentrically placed within said cavity in heat transfer relation with said coils, said encased fiber bundle comprising:
   a tapered center core with means defining a plurality of apertures adjacent a bottom end to allow fluid communication between the bottom anterior portion of said center core and said fiber bundle, said center core having an obstruction between opposing ends of said core preventing gas and fluid communication between said apertures in the opposite end of said core;

a plurality of hollow fibers wound on said tapered center core to form a tapered bundle of fibers with the fibers being open at the upper and lower ends thereof;

an interior housing enclosing the outside of said fiber bundle, said housing being tapered in a direction in an amount corresponding to the taper of said center core, the tapers on said interior housing and said center core cooperating to radially compress said fibers between said core and the abutting inside of said housing, said tapered interior housing having means defining a plurality of apertures adjacent the top end to provide fluid communication to said fiber bundle, the interior housing fiber bundle and center core being sealed at the ends thereof to define a gas flow path through the inside of said hollow fibers and to define a fluid flow path through said fiber bundle through said apertures in said housing and said center core, said interior housing cooperating with said casing to define a fluid flow path around the exterior of said coils with said housing positioned concentrically within said coils; and top and bottom caps cooperating with said outer casing and said bundles to define a gas flow path through said hollow fibers.

9. An oxygenator as defined in claim 8, wherein said fiber bundle further comprises:

a seal on one end of said fiber bundle; and resiliently mounted sealing means on an opposite end of said fiber bundle for sealing said fiber bundle interior housing with said h eat exchanger.

10. An oxygenator as defined in claim 8, further comprising:

means communicating with said apertures in said center core for removal of oxygenated fluid from said apertures.

11. An oxygenator as defined in claim 8, further comprising:

internally located fluid means communicating from the bottom of said center core to means defining a port on a top of said oxygenator to allow sampling of fluid after the fluid has passed through said fiber bundle.

12. An oxygenator as defined in claim 8, wherein said predetermined angle is about 2°.

13. An oxygenator as defined in claim 8, wherein said predetermined angle is between about 2° and 4°.

14. An oxygenator as defined in claim 8, wherein said predetermined angle is between about 2° and 6°.

15. An oxygenator as defined in claim 8, further comprising:

a fluid reservoir in fluid communication with said oxygenator; and adaptor means on said oxygenator for removably fastening said fluid reservoir to said oxygenator.

16. An oxygenator as defined in claim 8, wherein aid heat exchange coils each encircle said interior housing one and one-half times before diverging to terminate in said headers.

* * * * *